United States Patent [19]

Mohs

[11] Patent Number: 5,753,831
[45] Date of Patent: May 19, 1998

[54] GROUNDWATER SAMPLING DEVICE WITH A LIFT CHECK VALUE

[76] Inventor: Clifford E. Mohs, 1219 Pierce St. NE., Minneapolis, Minn. 55413

[21] Appl. No.: 813,222

[22] Filed: Mar. 7, 1997

[51] Int. Cl.⁶ .................................................. G01N 1/12
[52] U.S. Cl. .................................................. 73/864.63
[58] Field of Search ........................ 73/864.63, 864.65, 73/864.66; 251/319–326, 347; 137/430, 433

[56] References Cited

U.S. PATENT DOCUMENTS

| | | | |
|---|---|---|---|
| 743,787 | 11/1903 | Wickson | 251/323 |
| 857,703 | 6/1907 | Willmann | 137/433 |
| 1,204,635 | 11/1916 | Alexander | 137/433 |
| 2,486,729 | 11/1949 | Beckley | 251/319 |
| 2,938,388 | 5/1960 | Byrnes | 73/864.65 |
| 5,537,881 | 7/1996 | White | 73/864.63 |
| 5,566,576 | 10/1996 | Sher et al. | 73/864.65 |

FOREIGN PATENT DOCUMENTS

| | | | |
|---|---|---|---|
| 802309 | 7/1949 | Germany | 251/323 |

*Primary Examiner*—Robert Raevis
*Attorney, Agent, or Firm*—Patent Smart, PLLP; Claude T. Anderson

[57] ABSTRACT

A new lift check valve and groundwater sampling device using same is disclosed. The inventive device includes a body having a fluid flow bore extending therethrough and a first body end. A valve stem is sealingly disposed within the fluid flow bore and includes a first fluid flow bore extending from a first end and terminating at a disk integrally formed at a second end. The valve stem further includes a transverse bore extending therethrough in fluid flow communication with the first fluid flow bore and is moveable within the fluid flow bore between a first position in which the transverse bore is disposed without the fluid flow bore for fluid flow therethrough and a second position in which the transverse bore is disposed within the fluid flow bore to close off fluid flow through the fluid flow bore. A spring is provided to constrain the movement of the valve stem between the first and second positions including a first section fixedly attached to the disk and a second section extending perpendicularly from the first section and being receivable within an aperture formed in the valve stem. The second section is receivable within a peripheral recess formed in a base formed in the body opposite the first body. Alternativly a flared tab is provided to constraint the movement of the valve stem for use in single use applications.

13 Claims, 1 Drawing Sheet

GROUNDWATER SAMPLING DEVICE WITH A LIFT CHECK VALUE

BACKGROUND OF THE INVENTION

1. Field of the Invention

The present invention relates to lift check valves for controlling flow and more particularly pertains to a new groundwater sampling devices with lift check values into and out of a groundwater sampling device.

2. Description of the Prior Art

Groundwater pollution including that from volatile organic compounds (hereinafter VOC) continues to be a widespread problem in need of remediation. In order that samples of groundwater can be obtained, devices known as bailers are employed. Bailers are designed for single, disposable use or to be reusable. Known bailers include a narrow elongate tube having a ball check valve disposed at a lower end. The tube is lowered into a groundwater monitoring well and the ball check valve allows the groundwater being sampled to enter the tube but blocks the sample's exit from the tube when full or upon withdrawal from the well. Standard groundwater sampling protocol requires that three volumes of well water be removed prior to removal of a groundwater sample.

U.S Pat. No. 5,507,194 to Scavuzzo and Hawkins shows a known ball check valve that employs a ball and seat valve apparatus. While these valve apparatus are effective in allowing the sampled groundwater to enter the bailer tube, on many occasions particulates existent in the sampled groundwater interfere with the seating of the ball upon the seat and the sampled groundwater leaks from the tube.

Once the groundwater sample is collected, the bailer must be withdrawn from the well and raised to the surface. Prior art ball check valves employed in bailers are prone to lose their seal it jarred. Upon withdrawal from the well it is common for the bailer to jar against protuberances or offset seams in the well casing (wall). The resulting loss of sample not only makes sampling more difficult but also can lead to biasing of the concentration of VOC in the water to be sampled due to the turbulence induced by the escaping water. This turbulence drives off VOC. U.S. Pat. No. 5,404,949 to Voss attempts to remedy this problem by providing for top and bottom surfaces on the bailer tube that will not lodge against irregularities on the surface of well walls. The patent to Voss however teaches the use ol a ball and seat valve apparatus prone to sample loss as described above.

Another major problem encountered in groundwater sampling is low well water levels, for example, those that occur in the driest period of the year. Known prior art bailers will at most fill to the level of the well water surface. If this level is low, as for example only a few inches from the bottom, many samples must be taken to meet standard sampling quality control protocols. This problem together with the sample loss described above can compound quality control problems and make difficult the task of sampling groundwater.

Once the groundwater sample has been collected from the well for analysis, it must be removed from the bailer. Known prior art bailers employing a ball and seat valve apparatus suffer the disadvantage of not being easily emptied. U.S. Pat. No. 5,507,194 to Scuvuzzo and Hawkins teaches a disposable bailer employing a ball and seat apparatus. The sample is removed from the bailer by means of a pour spout disposed at an upper end of the bailer tube. Means are provided to constrain the longitudinal motion of the ball while the bailer is emptied but the ball must of necessity move during this operation thereby allowing sample to spill from the tube.

Thus it would be desirable to provide a valve for a groundwater sampling device that overcomes the deficiencies found in the prior art. It would also be desirable to provide a valve for a groundwater sampling device that reduces groundwater sample loss as the groundwater sampling device is withdrawn from the well. It would further be desirable to provide a valve that reduces sample loss due to the presence of particulates present in the sampled groundwater. It would also be desirable to provide a valve that can sample effectively at low well water levels. It would further be desirable to provide a valve which enables the sampled groundwater to be easily removed from the groundwater sampling device. It would further be desirable to provide a valve that is easily disassembled for cleaning. Finally, it would be desirable to provide a valve that is simple in design and easily manufactured as well as being reliable and of durable construction.

As will be more fully appreciated from the description that follows, the valve of the present invention has several advantages ever prior art check valves. A major advantage is the reduction of sample loss. This is accomplished by means of a first seal formed between a valve stem wall and a fluid flow bore. The contact surface between the valve stem wall and the fluid flow bore is of much greater dimension than that of the ball check valve and is thus less likely to leak sample if jarred upon withdrawal from the well during sample recovery.

Another major advantage of the valve of the present invention over prior art valves used in bailers is its ability to collect adequate samples even in situations where the water surface in the well is near the well bottom. This can be accomplished by alternately raising the bailer to shut the valve and then rapidly lowering the bailer below the water surface, thereby opening the valve and allowing liquid to enter the bailer. Thus, low water level wells can be quickly emptied with few withdrawals of the bailer from the well to achieve standard quality control protocols.

The valve of the present invention allows for controlled emptying from the bottom of the recovered bailer with a minimum of agitation, turbulence or likelihood of spills. This minimizes loss of VOC due to agitation that maintains sample integrity as well as exposure of personnel to spills of hazardous material.

Another advantage provided by the valve of the present invention is that cleaning and reuse of the valve can be easily accomplished if desired by removing the valve stem from the valve by simply removing a spring, pin or clip used as a stem retaining means. In addition the valve is sturdy, durable and easy to fabricate without sacrificing maximum potential flow rate into the bailer.

Finally the valve of the present invention reduces problems posed by particulates in the sample. A disk has a machined tapered edge that sealingly mates with a body tapered edge to prevent most particulates from being lodged in a second seal formed between the tapered edges. The machined surfaces are formed to direct particulates away from the second seal.

SUMMARY OF THE INVENTION

The present invention is a lift check valve for controlling the flow into and out of a groundwater sampling device.

The valve includes a body having a fluid flow bore extending therethrough and a first body end. A valve stem is

3 sealingly disposed within the fluid flow bore and includes a first fluid flow bore extending from a first end and terminating at a disk integrally formed at a second end. The valve stem further includes a transverse bore extending therethrough in fluid flow communication with the first fluid flow bore. The valve stem is moveable within the fluid flow bore between a first position in which the transverse bore is disposed at least slightly above the fluid flow bore to allow for fluid flow therethrough and a second position in which the transverse bore is disposed within the fluid flow bore to close off fluid flow through the fluid flow bore.

A means for constraining the movement of the valve stem within the fluid flow bore between the first and second positions is provided including a spring having a first section fixedly attached to the disk and extending through the first fluid flow bore and a second section extending perpendicular to the first section and extending through an aperture formed in the valve stem. Alternate means include a pin extending perpendicularly through the valve stem at the first end, a clip disposed at the first end and a flare or tab formed at the first end. The body further includes a base of greater peripheral dimension than the body disposed opposite the first body end and having a peripheral recess formed therein, the peripheral recess adapted to receive the second section of the spring, the pin, the clip or the flare or tab. Alternatively, the means for constraining the movement of the valve stem includes a stopping member disposed within a bailer tube interior, the stopping member determining the first position and obviating the need for a peripheral recess.

The body further includes a body tapered edge extending downwardly and outwardly, the body tapered edge being formed at the first body end. The body tapered edge matingly and sealingly receives a tapered edge extending downwardly and outwardly formed on the disk.

A means for sealingly mounting the lift check valve to a groundwater sampling device is provided. The groundwater sampling device includes a tube having an open end and a bottom end. The bottom end includes a threaded bore formed to threadingly and sealingly receive the lift check valve.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
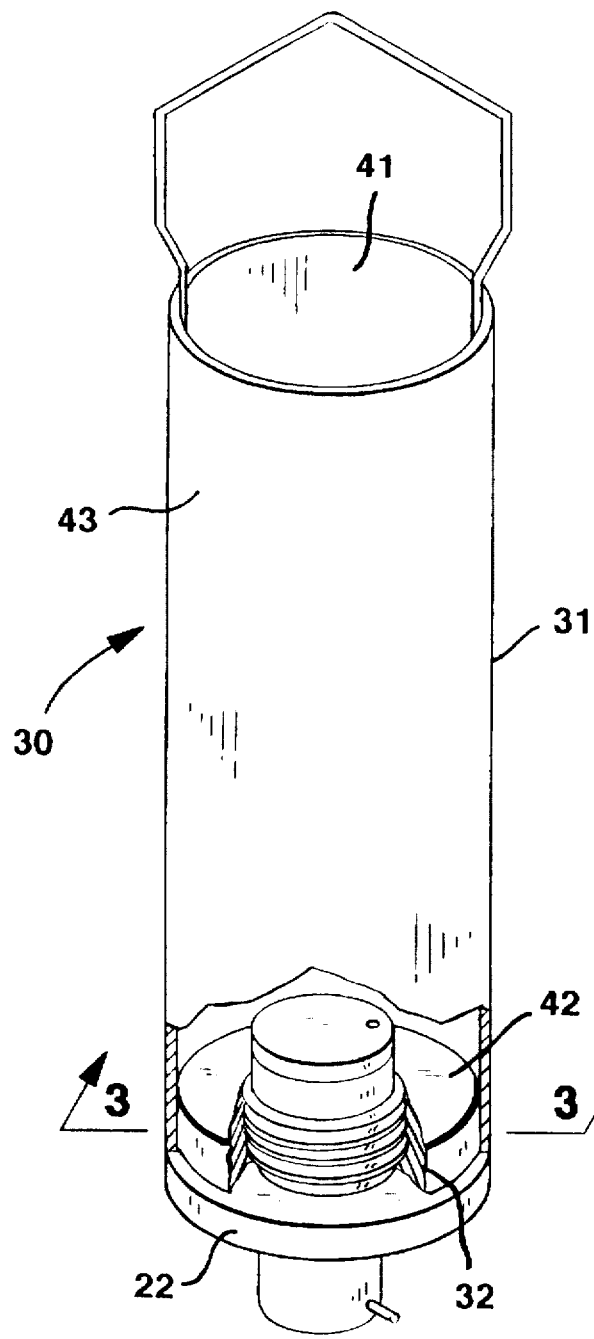
FIG. 1 is a partial cutaway perspective view of a groundwater sampling device showing the lift check valve of the present invention mounted thereon.
Figure 2:
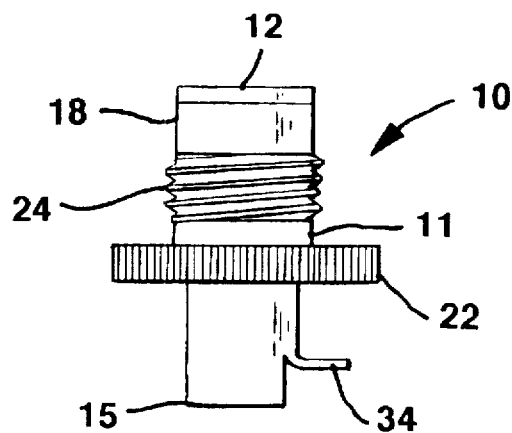
FIG. 2 is a side view of the lift check valve.
Figure 3:
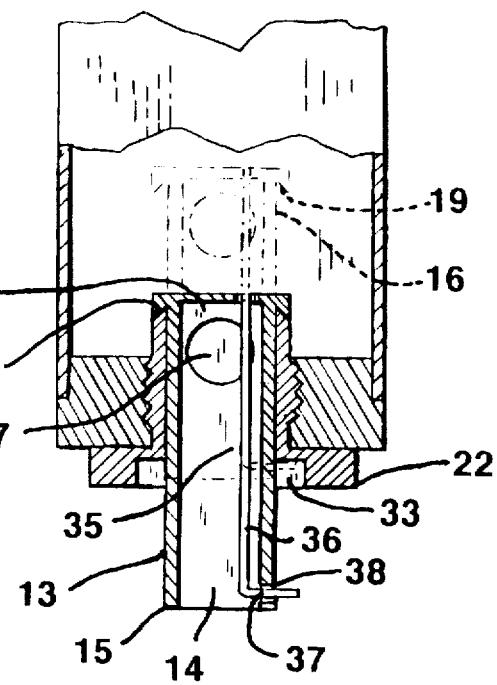
FIG. 3 is a cross sectional view taken along line 3—3 of FIG. 1.

With reference now to the drawings, and in particular to FIGS. 1 through 3 thereof, a new lift check valve embodying the principles and concepts of the present invention and generally designated by the reference numeral 10 will be described. Materials typically include stainless steel or Teflon™ and similar cholofluorocarbons for reusable applications or plastics such as polyethylene for single use applications.

More specifically, it will be noted that the lift check valve 10 comprises a body 11 having a fluid flow bore 23 extending therethiough and a first end 18. A valve stem 13 is sealingly disposed within the fluid flow bore 23 and includes a first fluid flow bore 14 extending from a first end 15 and terminating at a disk 12 integrally formed at a second end 16. The valve stem 13 further includes a transverse bore 17 extending therethrough in fluid flow communication with the first fluid bore 14. The valve stem 13 is moveable within the fluid flow bore 23 between a first position in which the transverse bore 17 is disposed without the fluid flow bore for fluid flow therethrough and a second positioin in which the transverse bore 17 is disposed within the fluid flow bore 23 to close off fluid flow through the fluid flow bore 23.

With reference to FIG. 1 the groundwater sampling device 30 includes a tube 31 having an open end 41, a bottom end 42 and an interior 43. The lift check valve 10 sealingly and threadingly mounts to the bottom end 42 that includes a threaded bore 32.

With reference to FIG. 2 the valve stem 13 is shown disposed within the body 11. The lift check valve 10 includes a valve stem 13 having a first end 15 and a disk 12 disposed at a second end 16. The body 11 includes a base 22 having a greater peripheral dimension than the body 11. The body also includes threads 24 formed thereon between the base 22 and a first body end 18. Also shown is a tab 34 formed from the valve stem first end 15 by cutting a section of the valve stem first end 15 and bending it out and away from the valve stem first end 15.

With reference to FIG. 3 the valve stem 13 includes a first fluid flow bore 14 that extends from the first end 15 and terminates at the disk 12 disposed at the second end 16. A transverse bore 17 extends through the valve stem 13 and is in fluid flow communication with the first fluid flow bore 14. In a first position the transverse bore 17 is disposed without the fluid flow bore 23 and fluid flow therethrough is allowed In a second position the transverse bore 17 is disposed within the fluid blow bore 23 to close off fluid flow through the fluid flow bore 23.

With continued reference to FIG. 3 an alternative means for constraining the movement of the valve stem between the first and second positions is shown including a spring 35 including a first section 36 fixedly attached to the disk 12 and extending through the first fluid flow bore 14. A second section 37 extends perpendicularly from the first section 36 and extends through an aperture 38 formed in the valve stem 13. A peripheral recess 33 formed in the base 22 receives the second section 37.

With further reference to FIG. 3 the first body end includes a body tapered edge 21 that extends downwardly and outwardly and matingly and sealingly receives a tapered edge 19 formed on the disk 12.

In use the groundwater sanipling device 30 is lowered into a well to collect a sample of groundwater. When liquid is encountered buoyant and other forces move the valve stem 13 to the first position thereby allowing for entry of groundwater into the tube interior 43. When fluid forces equalize, the valve stem 13 moves to the second position thereby closing off fluid flow. Valve stem 13 cannot be unseated by lateral forces due to the close tolerance between valve stem 13 and fluid flow bore 23. Furthermore a large upward force exrted upon the valve stem 13 is required before the transverse bore 17 is disposed above the tapered body edge 20 and fluid flow from the tube interior 43 is allowed.

As the tapered edge 19 matingly and sealingly meets the body tapered edge 21, fluid velocity increases between the two surfaces and moves any existent particulates away from the mating surfaces. Additionally, particulates are directed away from the valve stem 13. The particulates thus directed reside in a volume of the tube interior 43 formed by the elevation of the lift check valve 10 from the bottom end 42 and away from the seal formed by the body 11 and the valve stem 13.

Upon being withdrawn from the well the groundwater sampling device 30 is emptied by pressing the valve stem 13 onto the inside wall of a receiving container such that transverse bore 17 rises above the body tapered edge 21 to establish fluid flow communication In this manner the groundwater sampling device 30 can be partially or totally emptied. The flow is controlled by the position of the valve stem 13 relative to the transverse bore 17 and can be shut off at any moment to fill multiple sample receiving containers.

To clean the lift check valve 10 the second section 37 of the spring 35 is wholly fit into the first fluid flow bore 14 and the valve stem 13 is removed from the groundwater sampling device 30. In the case of the valve comprising the tab 34, it is contemplated that the sampling device would be designed for single use and thus there would be no need to remove the valve stem 13 from the first fluid flow bore 14.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A groundwater sampling device comprising:
    a tube having an open end adapted to be attached to a flexible line and a bottom end;
    a lift check valve sealingly attachable to the bottom end in fluid flow communication with an interior of the tube, the lift check valve comprising;
    a body having a fluid flow bore extending therethrough, and a first body end; and
    a valve stem sealingly disposed within the fluid flow bore, the valve stein having a first fluid flow bore extending from a first end and terminating at a disk integrally formed at a second end, the valve stem further having a transverse bore extending therethrough in fluid flow communication with the first fluid flow bore, the valve stem being moveable between a first position in which the transverse bore is disposed above the fluid flow bore allowing fluid flow therethrough and a second position in which the transverse bore is disposed within the fluid flow bore to close off fluid flow through the fluid flow bore.

2. The groundwater sampling device of claim 1 further comprising a means for constraining the movement of the valve between the first and second positions.

3. The groundwater sampling device of claim 2 wherein the body further comprises a base disposed opposite the first body end, the base having a peripheral recess formed therein; and
    wherein means for constraining the movement of the valve stem between the first and second positions further comprise a spring having a first section fixedly attached to the disk and extending through the first fluid bore and a second section extending perpendicular to the first section and being extendable through an aperture formed in the valve stem, the second section being extendable into the peripheral recess.

4. The groundwater sampling device of claim 2 wherein means for constraining the movement of the valve stem between the first and second positions further comprise a tab formed at the first end.

5. The groundwater sampling device of claim 1 wherein the disk further comprises a tapered edge extending downwardly and outwardly, the tapered edge being matingly and sealingly receivable by a body tapered edge formed at the first body end and extending downwardly and outwardly.

6. The groundwater sampling device of claim 1 wherein the body further comprises a base disposed opposite the first body end, the base being of greater peripheral dimension than the body and having a peripheral recess formed therein.

7. The groundwater sampling device of claim 1 wherein the body is cylindrical and is threadingly mountable to a threaded bore disposed through the bottom end.

8. A method of collecting water from a well in which the water level is less than the height of the groundwater sampling device, using the groundwater sampling device of claim 1, comprising the steps of:
    (A) lowering the groundwater sampling device into the well to allow water to flow through the lift check valve and into the tube;
    (B) rapidly raising the groundwater sampling device;
    (C) rapidly lowering the groundwater sampling device to allow additional water to flow through the lift check valve and into the tube;
    (D) repeating steps B and C to increase the amount of water in the groundwater sampling device;
    (E) removing the groundwater sampling device from the well; and
    (F) collecting a portion of the water into a sample container.

9. The method of claim 8 in which the step of collecting a portion of the water into a sample container further comprises;
    (A) gently pressing a sample container lip against the valve stem first end, thereby raising the valve stem such that the transverse bore is above the body tapered edge;
    (B) establishing fluid flow communication with the sample container; and
    (C) lowering the sample container from the valve stem, thereby closing the lift check valve.

10. A groundwater sampling device comprising:

a tube having an open end adapted to be attached to a flexible line and a bottom end;

a lift check valve sealingly attachable to the bottom end in fluid flow communication with an interior of the tube, the lift check valve comprising;

a body having a fluid flow bore extending therethrough, a first body end and a base, the base disposed opposite first body end, the base further being of greater peripheral dimension than the body and having a peripheral recess formed therein;

a valve stem sealingly disposed within the fluid flow bore, the valve stem having a first fluid flow bore extending from a first end and terminating at a disk integrally formed at a second end, the valve stem further having a transverse bore extending therethrough in fluid flow communication with the first fluid flow bore, the valve stem being moveable between a first position in which the transverse bore is disposed above the fluid flow bore for fluid flow therethrough and a second position in which the transverse bore is disposed within the fluid flow bore to close off fluid flow through the fluid flow bore, the disk further having a tapered edge extending downwardly and outwardly, the tapered edge being matingly and sealingly receivable by a body tapered edge formed at the first body end and extending downwardly and outwardly;

a means for constraining the movement of the valve between the first and second positions.

11. The groundwater sampling device of claim 10 wherein means for constraining the movement of the valve stem between the first and second positions further comprise a spring having a first section fixedly attached to the disk and extending through the first fluid bore and a second section extending perpendicular to the first section and being extendable through an aperture formed in the valve stem, the second section being extendable into the peripheral recess.

12. The groundwater sampling device of claim 11 wherein the body is cylindrical and is threadingly mountable to a threaded bore disposed through the bottom end.

13. The groundwater sampling device of claim 10 wherein means for constraining the movement of the valve stem between the first and second positions further comprise a tab formed at the first end.

\* \* \* \* \*